(12) United States Patent
Truckai

(10) Patent No.: US 11,304,594 B2
(45) Date of Patent: Apr. 19, 2022

(54) ARTICULATING MEDICAL DEVICE

(71) Applicant: Cirrus Technologies KFT, Budapest (HU)

(72) Inventor: Tamas J. Truckai, Saratoga, CA (US)

(73) Assignee: Meditrina, Inc., San Jose, CA (US)

( * ) Notice: Subject to any disclaimer, the term of this patent is extended or adjusted under 35 U.S.C. 154(b) by 576 days.

(21) Appl. No.: 15/419,723

(22) Filed: Jan. 30, 2017

(65) Prior Publication Data

US 2017/0215694 A1   Aug. 3, 2017

Related U.S. Application Data

(60) Provisional application No. 62/288,664, filed on Jan. 29, 2016.

(51) Int. Cl.
| | |
|---|---|
| *A61B 1/018* | (2006.01) |
| *A61B 1/00* | (2006.01) |
| *A61B 1/005* | (2006.01) |
| *A61M 25/01* | (2006.01) |
| *A61M 25/00* | (2006.01) |

(52) U.S. Cl.
CPC ............ *A61B 1/018* (2013.01); *A61B 1/0016* (2013.01); *A61B 1/0052* (2013.01); *A61B 1/0055* (2013.01); *A61B 1/0057* (2013.01); *A61B 1/00103* (2013.01); *A61B 1/00135* (2013.01); *A61B 1/00154* (2013.01); *A61M 25/0138* (2013.01); *A61M 25/0147* (2013.01); *A61M 25/0136* (2013.01); *A61M 25/0158* (2013.01); *A61M 2025/0003* (2013.01)

(58) Field of Classification Search
CPC ....... A61B 1/008; A61B 1/01; A61B 1/00135; A61B 1/00151; A61B 1/00154; A61B 2017/3445; A61B 2017/00296; A61B 2017/3447; A61M 25/0147; A61M 25/0136
USPC ................................................ 600/121–125
See application file for complete search history.

(56) References Cited

U.S. PATENT DOCUMENTS

| | | | | |
|---|---|---|---|---|
| 8,323,241 | B2 * | 12/2012 | Salahieh ........... | A61M 25/0138 604/95.04 |
| 8,469,880 | B2 * | 6/2013 | Herrmann .......... | A61B 1/00135 600/156 |
| 2008/0188868 | A1 * | 8/2008 | Weitzner .............. | A61B 1/0014 606/130 |
| 2012/0296168 | A1 * | 11/2012 | Horne, Jr. .......... | A61B 1/00071 600/121 |
| 2015/0011830 | A1 * | 1/2015 | Hunter ................. | A61B 1/0052 600/118 |

* cited by examiner

*Primary Examiner* — Alexandra L Newton
(74) *Attorney, Agent, or Firm* — Levine Bagade Han LLP

(57) ABSTRACT

Devices for use with introducers, endoscopes and catheters, where the devices relate to an articulating mechanism that allows a working end of a medical device to be steerable in order to access or visualize targeted sites in the interior of a patient's body.

18 Claims, 3 Drawing Sheets

ARTICULATING MEDICAL DEVICE

CROSS-REFERENCE TO RELATED APPLICATIONS

This application claims priority to U.S. Provisional Patent Application No. 62/288,664, filed on Jan. 29, 2016, the content of which is incorporated herein by reference in its entirety.

FIELD OF THE INVENTION

The present invention generally relates to medical devices such as introducers, endoscopes and catheters. More specifically, the devices and methods described herein relate to an articulating mechanism that allows a working end of a medical device to be steerable in order to access or visualize targeted sites in the interior of a patient's body.

DESCRIPTION OF THE RELATED ART

It is well known that there can be significant public health benefits from early diagnosis and treatment of disorders in sites in a patient's body that are accessible with an endoscope having a working channel. For example, endoscopes are used to diagnose and treat diseases in the urethra, bladder, ureter, kidney, uterus, nasal passageways, sinuses, esophagus, stomach, colon, lungs, bronchi and other body passageways.

A typical endoscope comprises a flexible sleeve with a fiber optic light guide that guides light from an external light source to the endoscope tip to illuminate the working space in the patient's body. Such an endoscope may have an imaging sensor and optics at its distal tip to produce an image that is routed to a display, or the endoscope my have an objective lens and fiber optic light guide that communicates with a camera detachably coupled to endoscope handle.

A typical flexible endoscope has a distal articulating portion, with articulation forces created in the handle which are transmitted to the articulation portion by control cables or pull-wires. The pull-wires allow the physician to steer the working end of the endoscope to direct and navigate the working end to visualize the targeted site. Endoscopes further included working channels for introducing treatment tools into a working space.

In commercial re-useable endoscopes, there are a number of problems. Flexible endoscopes are expensive devices and a paramount problem is sterilization of the endoscope following a procedure. Such sterilization requires tedious cleaning of the working channel with a brush followed by steam sterilization or another form of sterilization. Further, re-usable endoscopes are fragile and frequently damaged during use and particularly during the sterilization process.

Conventional articulating endoscopes also may be ineffective in performing articulation optimally. For example, elongated scopes may not be capable of transmitting significant torque from one end to the other, and instead tend to twist when torqued. The bending consistency of endoscope working ends may be far less than optimal since pull-wires can buckle an elongated shaft into a series of "S" shapes from tension on the pull-wire mechanisms. Further, the working end may not articulate in a flat plane or achieve the needed degree of angular deflection.

SUMMARY OF THE INVENTION

The present invention overcomes the problems with commercially available re-usable articulating endoscopes by providing a low cost disposable introducer or endoscope that is used only in a single procedure thereby eliminating the need for sterilization and repairs.

A particular embodiment of the present invention has an articulating mechanism that comprises first and second sleeves with slotted regions that are disposed adjacent one another. The first and second sleeves are fixed to one another at the distal tip of the device. Thus, axial translation of one sleeve relative to the other sleeve will articulate the working end.

In one variation, the present disclosure includes an articulating mechanism for use in a medical device. For example such a mechanism can include an elongated sleeve extending about an axis having a distal end and a distal slotted articulation portion; and a tensioning sleeve having a distal end and an interior channel extending therethrough, the tensioning sleeve located adjacent to the elongated sleeve, where the distal end of elongated sleeve and the distal end of the tensioning sleeve are coupled at a coupling portion to prevent relative movement of the tensioning sleeve and elongated sleeve at the coupling portion but to allow relative movement of the tensioning sleeve and elongated sleeve to permit articulation of the elongated sleeve and tensioning sleeve at the coupling portion.

A variation of the articulating mechanism where a proximal end of the elongated sleeve and a proximal end of the tensioning sleeve are carried in a handle and the handle includes an actuation mechanism that when moved causes relative axial movement between the elongated sleeve and the tensioning sleeve.

The articulating mechanism can comprise a manually moveable element selected from the group of sliders, triggers, levers, squeeze grips, syringe grips and rotating elements. Alternatively, or in combination, the actuation mechanism comprises a motor drive unit operatively coupled to at least one of the elongated sleeve and the tensioning sleeve. The motor drive unit can include a gear that engages the tensioning sleeve configured to provide axial movement. In an additional variation, the motor drive unit has at least one gear that engages the elongated sleeve and the tensioning sleeve configured to provide relative axial movement therebetween.

The devices and mechanism described herein can include an endoscopic device coupled to or in the device. Such an endoscopic device can be removable or affixed to the devices and/or mechanism. Variations of the mechanisms include one or more an open working channels. The devices described herein can include a first motor for axial movement of the elongated sleeve and a second motor for axial movement of the tensioning sleeve.

Variations of the devices can further include an EMI shielding layer surrounding the mechanism. In another variation, the devices described herein can include a first elongated sleeve with a distal end having a first slotted articulating portion; and a second elongated sleeve with a distal end having a second slotted articulating portion wherein a distal end of the first sleeve is affixed to a distal end of the second sleeve at a coupled portion to prevent relative movement of the first sleeve and second sleeve at the coupled portion; an actuation mechanism for moving the first and second sleeves relative to one another to thereby cooperatively articulate distal ends of the first sleeve and second sleeve. Aspects of this variation can be combined with features of additional variations of the device/mechanism as described herein.

DESCRIPTION OF THE INVENTION

The present invention relates to an articulation mechanism that can be used in the working end of steerable devices such as introducers, endoscopes and catheters. These medical devices allow an operator to access and view internal body anatomy of a patient as well as to insert surgical instruments into the working space. In addition, these devices may include integrated diagnostic and/or therapeutic capabilities to allow the operator to treat the patient in a single procedure. An articulation mechanism according to the present invention is quite simple and inexpensive and thus allows for the development of single-use, disposable devices.

Figure 1A:
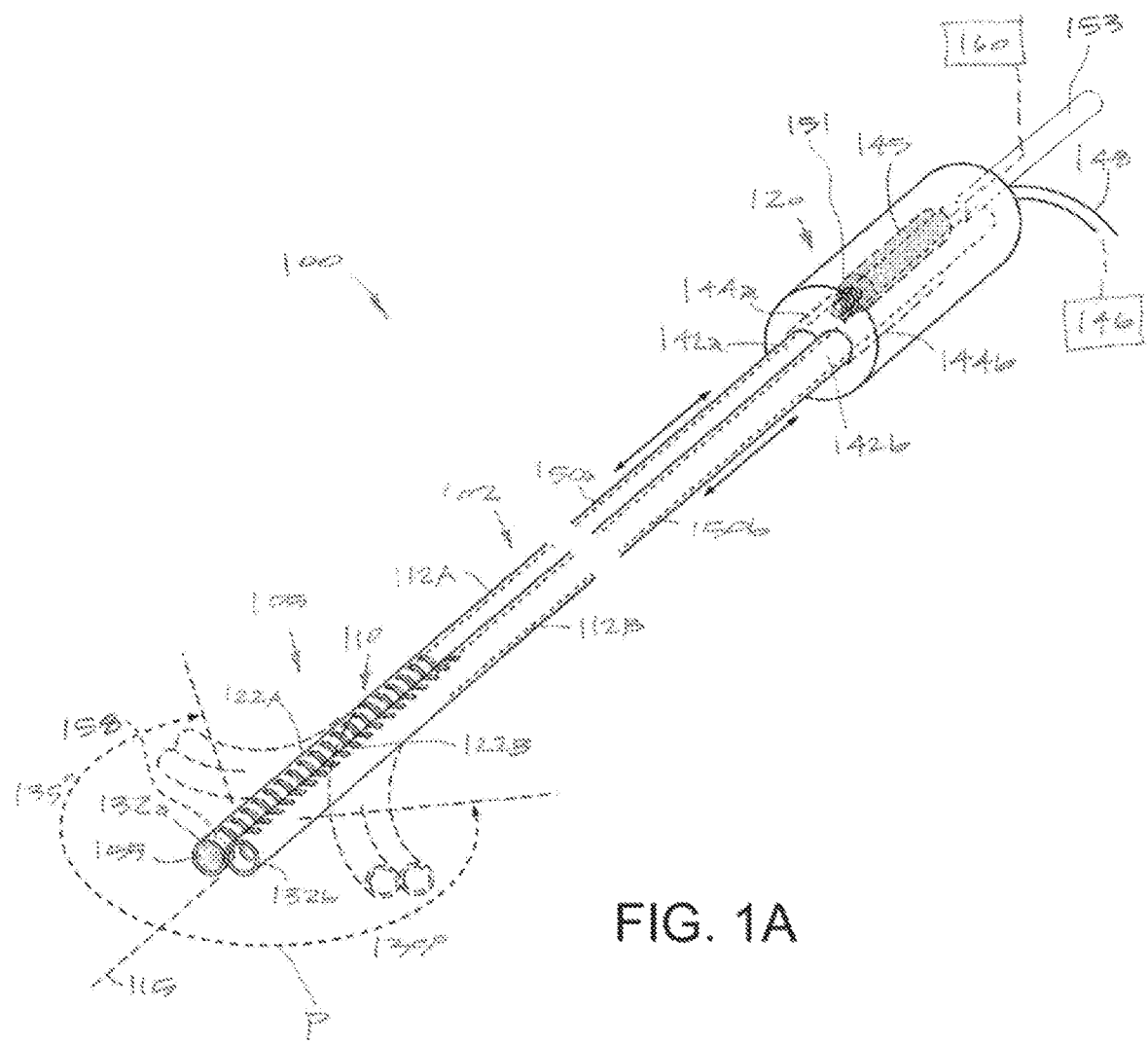
FIG. 1A illustrates a medical device with a working end having a form of an articulation mechanism including first and second slotted sleeves in accordance with an embodiment of the present invention.
Figure 2:
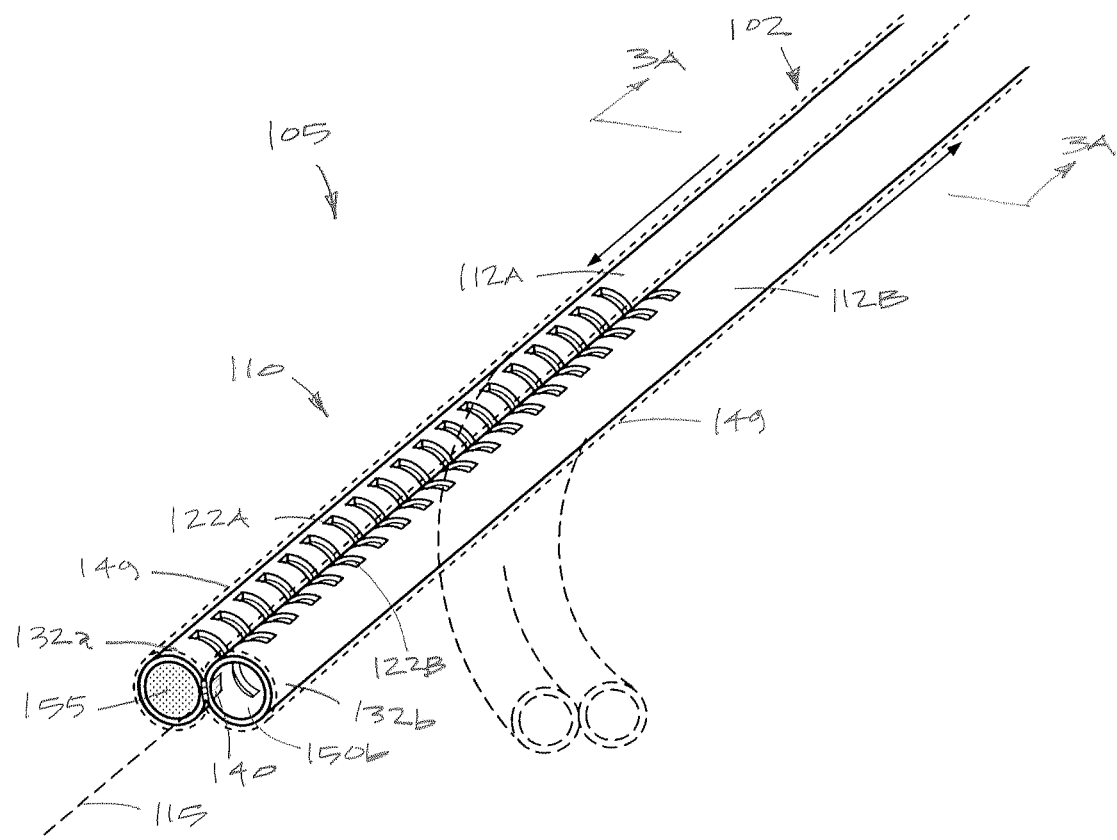
FIG. 2 depicts an enlarged view of the working end and articulation mechanism of FIG. 1.

In one variation shown in FIGS. 1A and 2, a steerable device 100 has an elongated shaft 102 and working end 105 with the articulation mechanism 110 corresponding to the invention. The shaft 102 has comprises first and second elongated sleeve 112A and 112B that extend about longitudinal axis 115 from handle 120 to the working end 105. Each sleeve 112A and 112B has a distal region that comprises a slotted sleeve portion 122A and 122B that can be articulated. Single slotted sleeve devices with pull-wires are known in the art. The sleeves typically can be thin-wall stainless steel or a similar metal, but polymer sleeves and composite polymer sleeves with metal elements therein also may be used. One advantage of the mechanism disclosed herein is that significant torque can be applied to the working end with very minimal unwanted twisting.

Each sleeve 112A and 112B can have a diameter that ranges from about 1 mm to 6 mm and in a particular embodiment, the sleeves can have similar or dissimilar diameters. In each sleeve, the slotted region 122A and 122B can be a similar length which can range from about 10 mm to 100 mm. As can be seen in FIG. 1A, the working end 105 is configured for articulation of about 135° from the longitudinal axis 115 in either direction, for a total of about 270° articulation in a plane P.

Figure 1B:
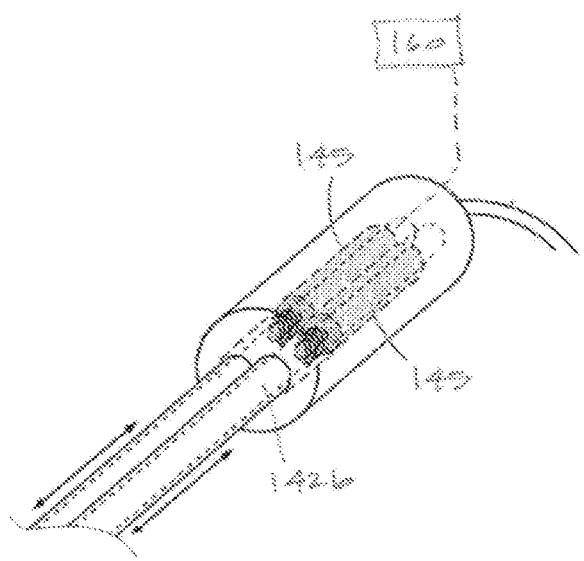
FIG. 1B illustrates a second motor coupled to a second sleeve.

Typically, the slotted regions 122A and 122B consist of very slots having a width of 0.1 mm to 2 mm with a center-to-center slot dimension ranging from about 0.5 mm to 2 mm such that the spaced apart slots provide the bending required to move the working end in the total of 270° articulation. As can be seen in FIG. 2, the distal tips 132a and 132b of the first and second sleeves are fixed to each other by a bond 140, which can be a weld, a pin, adhesive, fastener or the like. From FIGS. 1 and 2, it can be understood that axial movement of a first sleeve 112A relative to the second sleeve 112B will cause articulation of the distal end 105. One sleeve thus functions as a tensioning member relative to the other sleeve, with the term 'tensioning member' meaning that both pulling and pushing on a sleeve are possible to actuate the other sleeve. The proximal ends 142a and 142b of the first and second sleeves are disposed in channels 144a and 144b in the handle 120. In one variation, a motor drive unit 145 is coupled to at least one sleeve by a gear mechanism 151 (e.g., a worm gear) to move one or both sleeves axially relative to the handle 120.

By moving the first sleeve 112A relative to the second sleeve 112B longitudinally, the working end 105 thus can be articulated up to 135° in either direction. The working end can further include radiopaque markings or materials to allow viewing of the location of the working end under imaging.

In this variation, a motor drive unit 145 is provided in handle 120 which is coupled by a worm gear that engages a proximal portion of each sleeve to selectively move one sleeve relative to the other. In one variation, the motor drive unit 145 may move only one sleeve. In another variation, the motor drive unit may engage the first sleeve to move it distally while at the same time engaging the second sleeve to move it in the proximal direction. It is also possible to provide a motor drive unit comprising first and second motors with one motor configured to move the first sleeve and the second motor configures to move the second sleeve (See FIG. 1B).

The motor drive unit can use any type of motor, with a typical motor being a brushless electric motor coupled to an electrical source 146 through an electrical cable 148. In another variation, the articulating mechanism can manually operated to move a sleeve, for example, a slider-actuator, a trigger, a lever, a squeeze grip, a syringe grip, a rotating element or the like.

In FIG. 2, it should be appreciated that each of the sleeves 112A and 112B are covered in a very thin wall polymer coating or sleeve 149, such as silicone sleeve, which is adapted to prevent the slots of one sleeve from engaging or interfering with slots of the opposing sleeve when being articulated. Such a thin polymer surface between the sleeves 112A and 112B then allows for unimpeded relative axial movement between the sleeves.

It should be appreciated that each of the sleeves 112A and 112B has an interior channel 150a and 150b, and these interior channels can extend through the handle 120 (FIG. 1A). In one variation, a channel 150b comprises a working channel for introducing an elongates flexible probe into a surgical working space. In a variation, both the proximal ends in the distal ends of the interior channels 150a and 150b are open. In another variation, one channel is open-ended to function as a working channel and the other channel has a closed end with a transparent window 155 as shown in FIG. 2. In such an embodiment, a flexible endoscope 153 can be inserted into the closed-end channel to abut the transparent window 155. This variation would allow for using a flex-shaft endoscope that would not need to be sterilized.

In another variation, still referring to FIG. 1A, the first sleeve 112A has an interior channel 150a with a closed end and the transparent window 155 comprises a lens. Interior of the lens is an imaging chip 158 (e.g., a CMOS chip) with the cable that extends through the interior channel to an image processing unit and video display. A bundle of light fibers can also be provided in the interior channel 150a that can be coupled to light source 160. In another variation, LEDs can be provided in the distal end of channel 150a. The device 100 of FIG. 1 thus comprises a disposable endoscope with a working channel 150b with robust articulation means. The image display can be attached to the handle 120 or be separate from the handle and coupled to the image sensor by a cable or wireless means, such as Bluetooth.

Figure 3A:
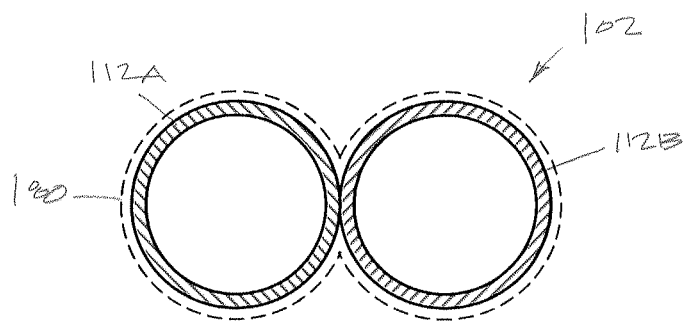
FIG. 3A is cross-section of the working end of FIG. 2 taken along line 3A-3A of FIG. 2.
Figure 3B:
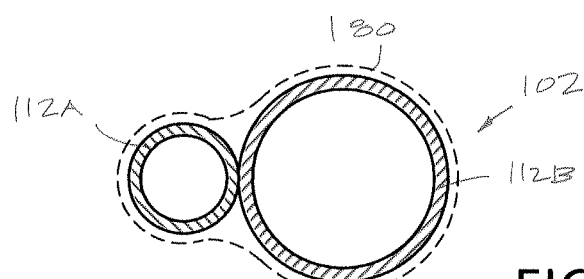
FIG. 3B is cross-section of another working end similar to that of FIG. 3A with different diameter first and second sleeves.

FIGS. 3A to 3D illustrate cross-sections of four different device shafts 102 which include additional fluid flow channels. FIG. 3A shows a cross-section of the device of FIG. 2. FIG. 3B shows a similar device but with different diameter first and second sleeves 112A and 112B.

Figure 3C:
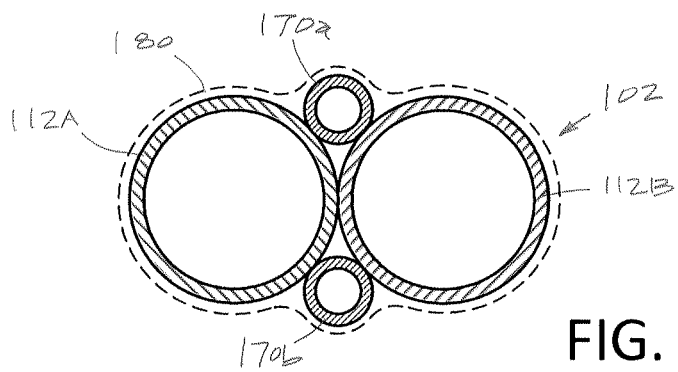
FIG. 3C is cross-section of another working end similar to that of FIG. 3A with additional open-end sleeves for pressure monitoring in a working space.
Figure 3D:
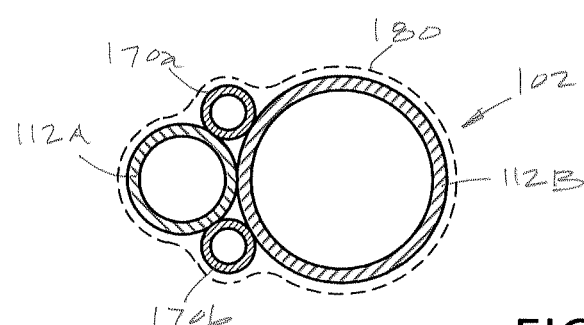
FIG. 3D is cross-section of another working end similar to that of FIG. 3B with two additional open-end sleeves for pressure monitoring.

FIG. 3C shows another variation with two large first and second sleeves in and two additional small diameter sleeves 170a and 170b which can be used for pressure monitoring for other purposes. In many procedures in urology and gynecology, it is useful or necessary to monitor fluid pressure in a working space when a fluid management system is used. It has been found that direct pressure monitoring with a fluid channel extending through the device to a remote pressure sensor is optimal. Another variation (not shown) can be is similar to that of FIG. 3C but with only one pressure monitoring sleeve 170a. FIG. 3D shows another variation similar to FIG. 3C with dissimilar sized first and second sleeves 112A and 112B together with two pressure monitoring sleeves 170 and 170b.

In another variation, the proximal portion of shaft 102 may have a larger diameter which then is necked down to a smaller cross-section working end. In another variation, the proximal portion of the elongated shaft 102 may comprise flexible catheter-like members that carry the working end 105. In any variation, an exterior sheath can surround the proximal region of the first and second sleeves to maintain the sleeves in a close, adjacent relationship.

In a method used, the device 100 may be used together with an elongated catheter or probe (not shown) that has an electrosurgical working end. When electrosurgical devices are used in close proximity to an imaging sensor as described above, there is a potential for electrical interference with the imaging chip. For that reason, another variation of the device includes electromagnetic interference shielding 180 (EMI shielding) shown in FIGS. 3A-3D that covers and surrounds the entire working end, shaft and handle. Electronic shielding is known in the art and can be a thin polymer layer layers with metallic powder or wire mesh components. Such shielding systems can be designed or provided by one of the following companies: Holland Shielding Systems BV, Jacobus Lipsweg 124, 3316BP Dordrecht, Netherlands; Optical Filters USA, 13447 South Mosiertown Road, Meadville Pa. 16335; or Parker Chomerics, 6 Flagstone Dr, Hudson, N.H. 03051.

A number of embodiments of the invention have been described. Nevertheless, it will be understood that various modifications may be made without departing from the spirit and scope of the invention.

What is claimed is:

1. An articulating mechanism for use in a medical device having a handle with a drive unit, the articulating mechanism comprising:
    an elongated sleeve extending from the handle about an axis and having a distal end and a distal slotted articulation portion; and
    a tensioning sleeve extending from the handle and having a distal end and an interior channel extending therethrough, the tensioning sleeve having a proximal portion configured to receive a force from the drive unit to cause movement of the proximal portion relative to the handle, the tensioning sleeve located adjacent to the elongated sleeve, where the distal end of the elongated sleeve and the distal end of the tensioning sleeve are coupled at a coupling portion to prevent relative movement of the tensioning sleeve and elongated sleeve at the coupling portion but to allow relative movement of a remaining portion of the tensioning sleeve and elongated sleeve in response to movement of the proximal portion to articulate the distal slotted articulation portion to permit articulation of the elongated sleeve and tensioning sleeve at the coupling portion.

2. The articulating mechanism of claim 1 where a proximal end of the elongated sleeve and a proximal end of the tensioning sleeve are carried in a handle and the handle includes an actuation mechanism that when moved causes relative axial movement between the elongated sleeve and the tensioning sleeve.

3. The articulating mechanism of claim 2 wherein the actuation mechanism comprises a motor drive unit operatively coupled to at least one of the elongated sleeve and the tensioning sleeve.

4. The articulating mechanism of claim 3 wherein the motor drive unit has a gear that engages the tensioning sleeve configured to provide axial movement.

5. The articulating mechanism of claim 3 wherein the motor drive unit has at least one gear that engages the elongated sleeve and the tensioning sleeve configured to provide relative axial movement therebetween.

6. The articulating mechanism of claim 1 further comprising an endoscopic device coupled to the elongated sleeve.

7. The articulating mechanism of claim 6 wherein the endoscopic device is removable from the elongated sleeve.

8. The articulating mechanism of claim 1 wherein the elongated sleeve has an open working channel.

9. The articulating mechanism of claim 1 further comprising an endoscopic device coupled to the tensioning sleeve.

10. The articulating mechanism of claim 9 where the endoscopic device is removable from the tensioning sleeve.

11. The articulating mechanism of claim 1 wherein the tensioning sleeve has an open working channel.

12. The articulating mechanism of claim 3 wherein the motor drive unit has a first motor for axial movement of the elongated sleeve and a second motor for axial movement of the tensioning sleeve.

13. The articulating mechanism of claim 1 further comprising an EMI shielding layer surrounding the articulating mechanism.

14. An articulating medical device, comprising:
    a handle;
    a first elongated sleeve with a distal end having a first slotted articulating portion, the first elongated sleeve extending from the handle;
    a second elongated sleeve with a distal end having a second slotted articulating portion, the second elongated extending from the handle, wherein a distal end of the first elongated sleeve is affixed to a distal end of the second elongated sleeve at a coupled portion to prevent relative movement of the first elongated sleeve and second elongated sleeve at the coupled portion; and
    an actuation mechanism coupled to the handle, where the actuation mechanism moves the first elongated sleeve and the second elongated sleeve at a proximal region relative to one another to thereby cooperatively articulate distal ends of the first elongated sleeve and second elongated sleeve.

15. The articulating mechanism of claim 14 wherein each of the first elongated sleeve and the second elongated sleeve have an open-ended or closed end interior channel.

16. The articulating mechanism of claim 13 wherein at least one of the first elongated sleeve and the second elongated sleeve has an open-ended end interior channel.

17. The articulating medical device of claim 14 further comprising an image sensor carried in a distal end of the first elongated sleeve.

18. The articulating medical device of claim 14 further comprising an EMI shielding layer surrounding at least the first elongated sleeve and the second elongated sleeve.

* * * * *